United States Patent [19]

Sirrenberg et al.

[11] Patent Number: 4,536,587
[45] Date of Patent: Aug. 20, 1985

[54] COMBATING PESTS WITH SUBSTITUTED BENZOYL-(THIO)UREAS

[75] Inventors: Wilhelm Sirrenberg, Sprockhoevel; Albrecht Marhold, Leverkusen; Ingeborg Hammann, Cologne; Ingomar Krehan, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 493,910

[22] Filed: May 12, 1983

Related U.S. Application Data

[63] Continuation of Ser. No. 268,961, Jun. 1, 1981, abandoned.

[30] Foreign Application Priority Data

Jun. 21, 1980 [DE] Fed. Rep. of Germany ....... 3023328

[51] Int. Cl.³ .................. C07D 319/14; C07D 317/44
[52] U.S. Cl. ...................................... 549/366; 549/439
[58] Field of Search ............... 549/366, 439; 424/278, 424/282

[56] References Cited

U.S. PATENT DOCUMENTS

| | | | |
|---|---|---|---|
| 3,639,668 | 2/1972 | Alles et al. | 424/278 |
| 3,748,331 | 7/1973 | Cooke et al. | 260/340.5 |
| 3,748,356 | 7/1973 | Wellinga et al. | 564/44 |
| 4,103,022 | 7/1978 | Sirrenberg et al. | 424/278 |
| 4,155,915 | 5/1979 | Arndt et al. | 260/340.5 |

FOREIGN PATENT DOCUMENTS 2123236 5/1971 Fed. Rep. of Germany.
2848794 5/1980 Fed. Rep. of Germany.

Primary Examiner—Ethel G. Love
Attorney, Agent, or Firm—Sprung Horn Kramer & Woods

[57] ABSTRACT

A compound of the formula

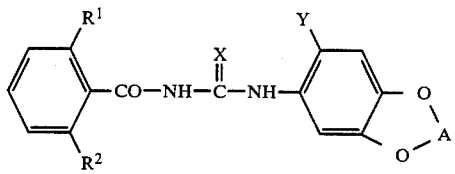

in which
$R^1$ represents a hydrogen or halogen atom or an alkyl radical,
$R^2$ represents a hydrogen or halogen atom,
X represents an oxygen or sulphur atom,
Y represents a hydrogen or halogen atom or an alkyl or halogenoalkyl radical and
A represents an alkylene radical which is substituted by fluorine and optionally additionally substituted by chlorine,
which possesses insecticidal activity.

15 Claims, No Drawings

COMBATING PESTS WITH SUBSTITUTED BENZOYL-(THIO)UREAS

This is a continuation of application Ser. No. 268,961 filed June 1, 1981, now abandoned.

The invention relates to certain new N-fluoroalkylenedioxy-phenyl-N'-benzoyl-(thio)ureas, to processes for their production and to their use as agents for combating pests, especially as insecticides.

It has already been disclosed that certain benzoylureas such as N-(4-chloro-phenyl)-N'-(2,6-difluorobenzoyl)-urea, N-(4-trifluoro-methoxy-phenyl)-N'-(2-chloro-benzoyl)-urea and N(2,2,4,4-tetrafluoro-1,3-benzoidoxin-6-yl)-N'-(2-chloro-benzoyl)-urea, have insecticidal properties (see German Offenlegungsschriften (German Published Specifications) No. 2,123,236, and U.S. Pat. Nos. 4,139,636 filed Feb. 13, 1979 and 4,103,022, filed July 25, 1978.

The present invention now provides, as new compounds, the substituted N-fluoroalkylenedioxy-phenyl-N'-benzoyl(thio)ureas of the general formula

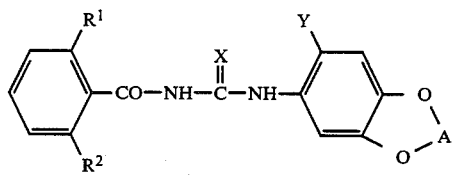
(I)

in which
$R^1$ represents a hydrogen or halogen atom or an alkyl radical,
$R^2$ represents a hydrogen or halogen atom,
X represents an oxygen or sulphur atom,
Y represents a hydrogen or halogen atom or an alkyl or halogenoalkyl radical and
A represents an alkylene radical which is substituted by fluorine and optionally additionally substituted by chlorine.

According to the present invention there is further provided a process for the production of a compound of the present invention, characterized in that
(a) a substituted benzoyl iso(thio)cyanate of the general formula

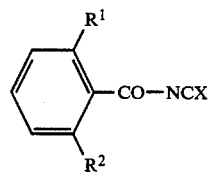
(II)

in which $R^1$, $R^2$ and X have the abovementioned meanings, is reacted with a fluoroalkylenedioxy-aniline of the general formula

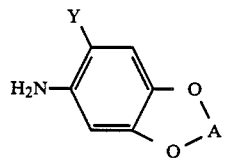
(III)

in which Y and A have the abovementioned meanings, if appropriate in the presence of a diluent, or
(b) a substituted benzamide of the general formula

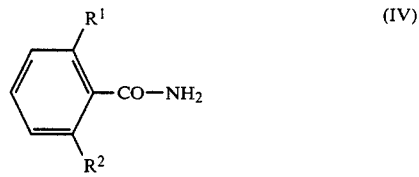
(IV)

in which $R^1$ and $R^2$ have the abovementioned meanings, is reacted with a fluoroalkylenedioxy-phenyl iso(thio)cyanate of the general formula

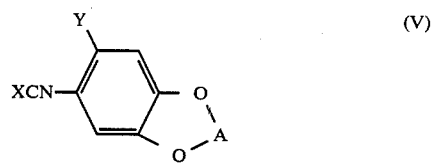
(V)

in which X, Y and A have the abovementioned meanings, if appropriate using a diluent; and the end product of the formula (I) formed by reaction variant (a) or (b) is isolated.

The new compounds of the formula (I) have properties which enable them to be used as agents for combating pests, and, in particular, they are distinguished by an outstanding insecticidal activity.

Surprisingly, the N-fluoroalkylenedioxy-phenyl-N'-benzoyl-ureas of the formula (I) have a considerably more powerful insecticidal action than the compounds known from the state of the art.

In the definition of $R^1$ and Y, "alkyl" preferably denotes a straight-chain or branched alkyl radical with 1 to 6, preferably 1 to 4, carbon atoms. Examples which may be mentioned are methyl, ethyl, n- and i-propyl, n-, i- and t-butyl, n-pentyl and n-hexyl radicals. Methyl and ethyl radical, in particular a methyl radical, may be mentioned as preferred.

In the halogenoalkyl radical of Y, the alkyl group preferably has the same meaning as in the case of above preferred meaning for "alkyl" in $R^1$ and Y, it being possible for the alkyl group to be substituted by 1 or more, preferably 1 to 5 and in particular 1 to 3, identical or different halogen atoms. The CF₃ group is very particularly preferred.

The alkylene radical of A preferably contains 1 to 3, in particular 1 or 2, carbon atoms. Alkylene A is generally substituted by 1 to 4, preferably 2 or 3, fluorine atoms and is optionally additionally preferably substituted by 1 or 2, in particular 1, chlorine atom.

The halogen atoms of $R^1$, $R^2$ and Y generally represent fluorine, chlorine, bromine or iodine atoms, preferably a fluorine, chlorine or bromine atom and in particular fluorine or chlorine atoms.

Accordingly, preferred compounds of the present invention are those in which
$R^2$ and X have the meanings given in the definition of compounds of the invention,
$R^1$ represents a hydrogen or halogen atom or an alkyl radical with 1 to 6 carbon atoms,
Y represents a hydrogen or halogen atom, or an alkyl radical with 1 to 6 carbon atoms or a halogenoalkyl radical with 1 to 6 carbon atoms and 1 to 5 halogen atoms and A represents an alkylene radical which has 1 to 3 carbon atoms and is substituted by fluorine and optionally additionally substituted by chlorine.

Particularly preferred compounds of the present invention are those in which R¹ represents a fluorine, chlorine, bromine or iodine atom or a methyl radical, R² represents a hydrogen, fluorine, chlorine, bromine or iodine atom, X represents an oxygen or sulphur atom, Y represents a hydrogen or chlorine atom or a methyl or trifluoromethyl radical and A represents an alkylene radical which has up to 2 carbon atoms and is substituted by fluorine and optionally substituted by chlorine.

Especially preferred compounds of the present invention are those in which $R^1$ represents a fluorine, chlorine, or bromine atom or a methyl radical, $R^2$ represents a hydrogen, fluorine, or chlorine atom, X represents an oxygen or sulphur atom, Y represents a hydrogen or chlorine atom or a methyl or $CF_3$ radical, and especially represent a hydrogen atom, and A represents a difluoromethylene radical or an ethylene radical which is substituted by 3 or 4 fluorine atoms or by 3 fluorine atoms and 1 chlorine atom.

If, for example, 2fluoro-benzoyl isothiocyanate and 3,4-(tetrafluoroethylenedioxy)-aniline are used as starting substances in reaction variant (a) and 2,6-dibromo-benzamide and 3,4-(difluoromethylenedioxy)-phenyl isocyanate are used as the starting substances in reaction variant (b), the processes according to the present invention are illustrated by the following equations:

Reaction Variant (a)

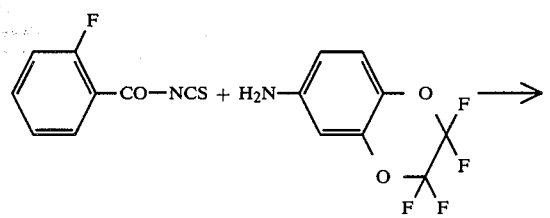

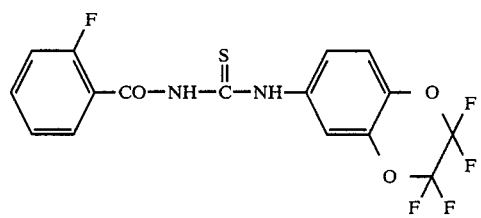

Reaction Variant (b)

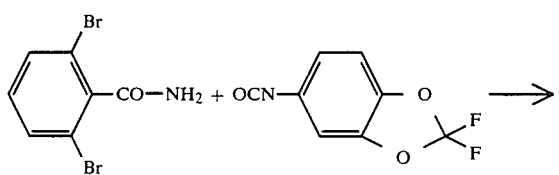

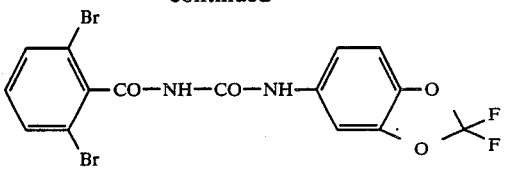

Preferred starting substances of the formula (II) and (III), or (IV) and (V) to be used in reaction variants (a) and (b) are those in which, $R^1$, $R^2$, X, Y and A respectively represent those radicals which have been mentioned in the definition of the preferred, particularly preferred and especially preferred compounds of the present invention.

Benzoic acid amides of formula (IV) to be used as starting compounds and the corresponding benzoyl iso-(thio)cyanates of formula (II) are known and can be prepared by generally customary methods, by processes analogous to known processes (see, for example, J. Org. Chem. 30, (1965), 4306–4307 and DE-AS (German Published Specification) No. 1,215,144).

Examples which may be mentioned are: 2-fluoro-2-chloro-, 2-bromo-, 2-iodo-, 2-methyl-, 2,6-difluoro-, 2,6-dichloro-, 2,6-dibromo- and 2-chloro-6-fluoro-benzoic acid amide; 2-fluoro-, 2-chloro-, 2-bromo-, 2-iodo-, 2-methyl-, 2,6-difluoro-, 2,6-dichloro-, 2,6-dibromo-, and 2-chloro-6-fluoro-benzoyl isocyanate; and 2-fluoro-, 2-chloro-, 2-bromo-, 2-iodo-, 2-methyl-, 2,6-difluoro-, 2,6-dichloro-, 2,6-dibromo- and 2-chloro-6-fluoro-benzoyl isothiocyanate.

Fluoroalkylenedioxy-anilines of formula (III) also to be used as starting substances and the corresponding fluoroalkylenedioxy-phenyl iso-(thio)cyanates (V) are likewise known and can be prepared by generally customary methods, by processes analogous to known processes (see German Offenlegungsschrift (German Published Specification) No. 2,848,531).

Examples which may be mentioned are: 5-amino-, 5-isocyanato- and 5-isothiocyanato-2,2-difluoro-1,3-benzodioxole, 5amino-, 5-isocyanato- and 5-isothiocyanato-6-chloro-2,2-difluoro-1,3-benzodioxole, 5-amino-, 5-isocyanato- and 5-isothiocyanato-6-methyl-2,2-difluoro-1,3-benzodioxole, 5-amino-, 5-isocyanato- and 5-isothiocyanato-6-trifluoromethyl-2,2-difluoro-1,3-benzodioxole, 6-amino-, 6-isocyanato- and 6-isothiocyanato-2,2-difluoro-1,4-benzodioxin, 6-amino-, 6-isocyanato- and 6-isothiocyanato-2,2,3-trifluoro-1,4-benzodioxin, 6-amino-, 6-isocyanato- and 6-isothiocyanato-7-chloro-2,2,3-trifluoro-1,4-benzodioxin, 6-amino-, 6-isocyanato- and 6-isothiocyanato-7-methyl-2,2,3-trifluoro-1,4-benzodioxin and 6-amino-, 6-isocyanato- and 6-isothiocyanato-7-trifluoromethyl-2,2,3-trifluoro-1,4-benzodioxin.

Both process variants for the preparation of the new N-fluoroalkylenedioxy-phenyl-N'-benzoyl-(thio)ureas of the present invention are preferably carried out using diluents.

Possible diluents are virtually any of the inert organic solvents. These include, in particular, aliphatic and aromatic, optionally halogenated hydrocarbons (such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ethyl acetate), nitriles, (such as acetonitrile and propionitrile), amides (such as dimethylformamide, dimethylacetamide and N-methyl-pyrrolidone), dimethylsulphoxide, tetramethylene sulphone and hexamethylphosphoric acid triamide.

The reaction temperature can be varied within a substantial range. In general, the reaction is carried out at a temperature between 20° and 180° C., preferably at between 60° to 120° C. The process variants according to the invention are in general carried out under normal pressure.

The starting substances are usually employed in equimolar amounts for carrying out the process variants according to the invention. An excess of either of the reactants provides no substantial advantages. The reaction is in general carried out in a suitable diluent and the reaction mixture is stirred at the required temperature for several hours. Thereafter, the reaction mixture is allowed to cool and, in the case where the end products are sparingly soluble in the solvent used, the product which has crystallized out is filtered off. The products are otherwise isolated and, if appropriate, purified by generally customary methods, for example by evaporating off the solvent (if appropriate under reduced pressure). They are characterized by their melting point.

As already stated, in addition to the new compounds the present invention and their production, the present invention also relates to pest-combating agents which contain compounds of the present invention, the preparation of these pest-combating agents and their use. The compounds of the present invention also exhibit a fungicidal activity, which increases their value when used in plant protection as pest-combating agents.

The active compounds are well tolerated by plants, have a favorable level of toxicity to warm-blooded animals, and are suitable for combating animal pests, especially insects, arachnida and nematodes, and very particularly preferentially for combating insects, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;*
from the class of the Diplopoda, for example *Blaniulus guttulatus;*
from the class of the Chilopoda, for example *Geophilus carpophagus* and Scutigera spec.;
from the class of the Symphyla, for example *Scutigerella immaculata;*
from the order of the Thysanura, for example *Lepisma saccharina;*
from the order of the Collembola, for example *Onychiurus armatus;*
from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;*
from the order of the Dermaptera, for example *Forficula auricularia;*
from the order of the Isoptera, for example Reticulitermes spp.;
from the order of the Anoplura, for example *Phylloxera vastatrix,* Pemphigus spp., *Pediculus humanus corporis,* Haematopinus spp. and Linognathus spp.;
from the order of the Mallophaga, for example Trichodectes spp. and Damalinea spp.;
from the order of the Thysanoptera, for example *Hercinothrips femoralis* and *Thrips tabaci;*
from the order of the Heteroptera, for example Eurygaster spp., *Dysdercus intermedius, Piesma quadrata, Cimex lectularius, Rhodnius prolixus* and Triatoma spp.;
from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and Psylla spp.;
from the order of the Lepidoptera, for example *Pectinophora gossypiella, Eupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana, Heliothis* spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;*
from the order of the Coleoptera, for example *Anobium punctatum, Rhizopertha dominica, Bruchidius obtectus, Acanthoscelides obtectus, Hylotrupes bajulus, Agelastica alni, Leptinotarsa decmineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis. Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;*
from the order of the Hymenoptera, for example Diprion spp., Hoplocampa spp., Lasius spp., *Monomorium pharaonis* and Vespa spp.;
from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;*
from the order of the Siphonaptera, for example *Xenopsylla cheopis* and Ceratophyllus spp.;
from the class of the Arachnida, for example *Scorpio maurus* and *Latrodectus mactans;*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphide waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 1% by weight.

The compounds may be employed in a customary manner appropriate for the particular use forms.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture witn synergistic agents. Synergistic agents are compounds which increase the action of the active compounds, without it being necessary for the synergistic agent added to be active itself.

When used against pests harmful to health and pests of stored products, the active compounds are distinguished by an excellent residual action on wood and clay as well as a good stability to alkali on limed substrates.

The active compounds according to the invention are also suitable for combating ectoparasites and endoparasites, preferably ectoparasitic insects, in the field of veterinary medicine and in the field of animal husbandry.

In this context, the active compounds according to the invention are used in a known manner, such as by oral administration, for example in the form of tablets, capsules, drinks and granules, by dermal application, for example in the form of dipping, spraying, pouring on and spotting on, and dusting, and by parenteral administration, for example in the form of an injection.

The new compounds of the present invention can accordingly also be particularly advantageously used in animal husbandry (for example cattle, sheep, pigs and poultry, such as hens and geese). In a preferred embodiment of the invention, the new compounds are administered to the animals orally, if appropriate in the form of suitable formulations (see above) and if appropriate with the drinking water or feed. Since they are eliminated in an effective manner in the droppings, it is in this way very simple to prevent the developments of insects in the animal droppings. The dosages and formulations suitable in each case depend, in particular, on the nature and development stage of the useful animals and also on the degree of infestation by the insects, and can easily be determined and established by customary methods. In the case of cattle, the new compounds can be used, for example, in dosages of 0.01 to 1 mg/kg of body weight.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids, or nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention also provides a method of combating insects which develop in animal droppings, which comprises administering orally to the animal a compound of the present invention alone or in admixture with a diluent or carrier.

The present invention further provides crops protected from damage by pests being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The preparation of the compounds according to the invention will be illustrated by the following examples:

EXAMPLE 1

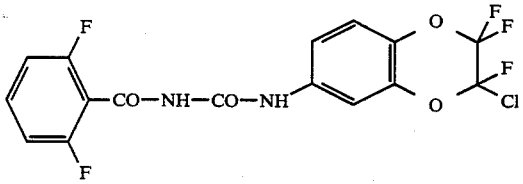
(1)

3.66 g (0.02 mole) of 2,6-difluorobenzoyl isocyanate in 20 ml of toluene were added to a solution of 4.8 g (0.02 mole) of 6-amino-2,2,3-trifluoro-3-chloro-1,4-benzodioxin in 40 ml of toluene at 60° C. The batch was stirred for one hour at 80° C. and was then cooled to room temperature. The substance which had precipitated was filtered off, washed with a little toluene and dried. 8.3 g (98% of theory) of product with a melting point of 197° C. were obtained.

EXAMPLE 2

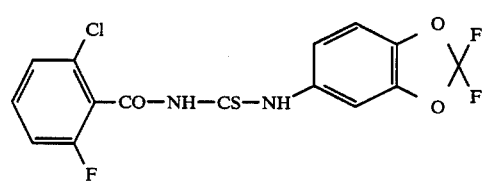
(2)

A solution of 4.3 g (0.02 mole) of 2-chloro-6-fluorobenzoyl isothiocyanate in 10 ml of toluene was added to a solution of 3.46 g (0.02 mole) of 5-amino-2,2-difluorobenzodioxole in 40 ml of toluene at 60° C. and the batch was stirred at 80° C. for one hour. Thereafter, it was cooled to room temperature and the substance which had precipitated was filtered off. After drying, 7.4 g (95% of theory) of product with a melting point of 174° C. were obtained.

EXAMPLE 3

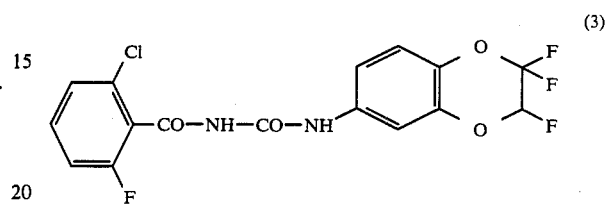
(3)

6.93 g (0.03 mole) of 6-isocyanato-2,2,3-trifluoro-1,4-benzodioxin were added to a solution, warmed to 100° C., of 5.22 g (0.03 mole) of 2-chloro-6-fluoro-benzamide in 80 ml of toluene and the batch was stirred at 100° C. for 28 hours. On cooling to room temperature, the substance precipitated. It was filtered off and dried, and had a melting point of 194° C. Yield: 7.5 g (61.5% of theory). The compound was identical to a sample prepared by process variant (a).

The compounds listed in the following tables were also prepared according to Examples 1 to 3, by an analogous procedure, process variants (a) and (b) being applied in the same manner.

TABLE 1

Compounds of the formula (Ia)

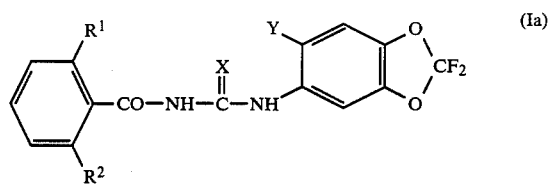
(Ia)

| Compound No. | $R^1$ | $R^2$ | Y | X | Melting point °C. |
|---|---|---|---|---|---|
| 4 | H | H | H | O | 217 |
| 5 | F | H | H | O | 167 |
| 6 | Cl | H | H | O | 202 |
| 7 | Br | H | H | O | 201 |
| 8 | I | H | H | O | 196 |
| 9 | $CH_3$ | H | H | O | 200 |
| 10 | Cl | Cl | H | O | 205 |
| 11 | Cl | F | H | O | 221 |
| 12 | F | F | H | O | 220 |
| 13 | Cl | H | $CF_3$ | O | 156 |
| 14 | Cl | F | $CF_3$ | O | 130 |
| 15 | F | F | $CF_3$ | O | 181 |
| 16 | Cl | H | Cl | O | 215 |
| 17 | Br | H | Cl | O | 213 |
| 18 | Cl | Cl | Cl | O | 265 |
| 19 | Cl | F | Cl | O | 247 |
| 20 | F | F | Cl | O | 228 |
| 21 | Cl | H | H | S | 158 |
| 22 | Cl | H | $CF_3$ | S | 172 |
| 23 | Cl | H | Cl | S | 133 |
| 24 | Cl | Cl | Cl | S | 197 |
| 25 | Cl | F | Cl | S | 174 |
| 26 | F | F | Cl | S | 156 |

TABLE 1-continued

Compounds of the formula (Ia)

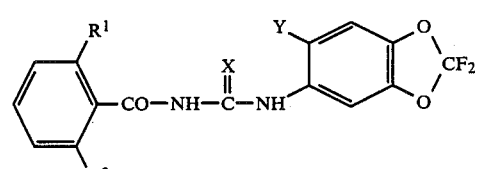

| Compound No. | R¹ | R² | Y | X | Melting point °C. |
|---|---|---|---|---|---|
| 27 | F | F | H | S | |

TABLE II

Compounds of the formula (Ib).

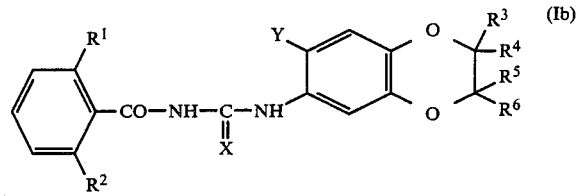

| Compound No. | R¹ | R² | R³ | R⁴ | R⁵ | R⁶ | Y | X | Melting point °C. |
|---|---|---|---|---|---|---|---|---|---|
| 28 | Cl | H | F | F | H | H | H | O | 183 |
| 29 | Br | H | F | F | H | H | H | O | 177 |
| 30 | Cl | Cl | F | F | H | H | H | O | 227 |
| 31 | Cl | F | F | F | H | H | H | O | 201 |
| 32 | F | F | F | F | H | H | H | O | 214 |
| 33 | Cl | H | F | F | F | H | H | O | 186 |
| 34 | Br | H | F | F | F | H | H | O | 170 |
| 35 | Cl | F | F | F | F | H | H | O | 198 |
| 36 | Cl | H | F | F | F | Cl | H | O | 184 |
| 37 | Br | H | F | F | F | Cl | H | O | 183 |
| 38 | CH₃ | H | F | F | F | Cl | H | O | 164 |
| 39 | Cl | Cl | F | F | F | Cl | H | O | 210 |
| 40 | F | H | F | H | F | F | CH₃ | O | 203 |
| 41 | Cl | H | F | H | F | F | CH₃ | O | 148 |
| 42 | Cl | Cl | F | H | F | F | CH₃ | O | 215 |
| 43 | Cl | F | F | H | F | F | CH₃ | O | 169 |
| 44 | F | F | F | H | F | F | CH₃ | O | 198 |
| 45 | F | H | F | H | F | F | Cl | O | 168 |
| 46 | Br | H | F | H | F | F | Cl | O | 180 |
| 47 | CH₃ | H | F | H | F | F | Cl | O | 187 |
| 48 | Cl | Cl | F | H | F | F | Cl | O | 231 |
| 49 | F | F | F | H | F | F | Cl | O | 206 |
| 50 | Cl | H | F | F | H | H | H | S | 128 |
| 51 | Cl | Cl | F | F | H | H | H | S | 189 |
| 52 | Cl | F | F | F | H | H | H | S | 158 |
| 53 | F | F | F | F | H | H | H | S | 137 |
| 54 | Cl | H | F | F | F | H | H | S | 116 |
| 55 | Cl | Cl | F | F | F | H | H | S | 158 |
| 56 | Cl | F | F | F | F | H | H | S | 146 |
| 57 | Cl | H | F | F | F | Cl | H | S | 148 |
| 58 | Cl | F | F | F | F | Cl | H | S | 193 |
| 59 | F | F | F | F | F | Cl | H | S | 175 |
| 60 | Cl | H | F | H | F | F | CH₃ | S | 173 |
| 61 | Cl | F | F | H | F | F | CH₃ | S | 205 |
| 62 | Cl | Cl | F | H | F | F | Cl | S | 202 |
| 63 | F | F | F | H | F | F | Cl | S | 186 |

The activity of the compounds of this invention is illustrated by the following examples wherein the compounds according to the present invention are each identified by the number (given in brackets) from the preparative examples and tables hereinabove:

EXAMPLE 4

Plutella test

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of active compound of the desired concentration and were infested with caterpillars of the diamond-back moth (*Plutella maculipennis*), as long as the leaves were still moist.

After the specified periods of time, the destruction in % was determined. 100% meant that all the caterpillars had been killed; 0% meant that none of the caterpillars had been killed.

In this test, for example, in an experiment with an active compound concentration of 0.001%, compounds (1), (2), (11), (12), (27), (32) to (38), (49), (53), (56) to (59) and (63) exhibited a degree of destruction of 100% after 7 days.

EXAMPLE 5

Laphygma test

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all the caterpillars had been killed; 0% meant that none of the caterpillars had been killed.

In this test, for example, in an experiment with an active compound concentration of 0.001%, the following compounds (1), (2), (6), (7), (10) to (12), (20), (21), (27), (31), (33), (35) to (39), (44), (49) and (57) to (59) exhibited a degree of destruction of 100% after 7 days.

EXAMPLE 6

Mosquito larvae test

Test insects: *Aedes aegypti*
Solvent: 99 parts by weight of acetone
Emulsifier: 1 part by weight of benzyl hydroxydiphenyl glycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of active compound of the desired concentration were filled into glass vessels and about 25 mosquito larvae were then placed in each glass vessel.

After 21 days, the degree of destruction in % was determined. 100% meant that all the larvae had been killed.

In this test, for example, in an experiment with dilutions of $10^{-3}$ to $10^{-4}$ ppm, compounds (1), (36), (39) and (59) exhibited a degree of destruction of 100% in 21 days.

EXAMPLE 7

Test with *Lucilia cuprina res.* larvae

Solvent: 35 parts by weight of ethylene glycol monomethyl ether, 35 parts by weight of nonylphenol polyglycol ether To produce a suitable preparation of active compound, three parts by weight of active compound were mixed with seven parts by weight of the abovementioned solvent mixture and the concentrate thus obtained was diluted with water to the particular desired concentration.

About 20 *Lucilia cuprina res.* larvae were introduced into a test tube which contained approx. 1 cm² of horse flesh and 0.5 ml of the preparation of active compound. After 24 hours, the degree of destruction was determined.

In this test, for example in an experiment with an active compound concentration of 100 ppm, compounds (6), (10) to (12), (28), (31), (33) to (35), (54), (55), (57) and (59) exhibited degrees of destruction of between 50 and 100%.

It will be appreciated that the instant specification and examples are set forth by way of illustration and not limiation, and that various modifications and changes may be made without departing from the spirit and scope of the present invention.

We claim:

1. A compound of the formula

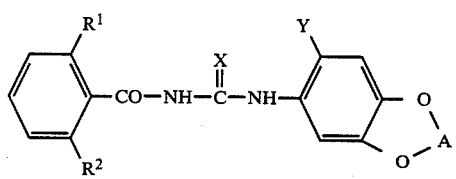

in which
R¹ represents a hydrogen or halogen atom or an alkyl radical,
R² represents a hydrogen or halogen atom,
X represents an oxygen or sulphur atom,
Y represents a hydrogen or halogen atom or an alkyl or halogenoalkyl radical and
A represents a C₁₋₂-alkylene radical which is substituted by fluorine and optionally additionally substituted by chlorine, with the proviso that when A is ethylene at least one of R¹ and R² must be halogen.

2. A compound according to claim 1, in which
R¹ represents a hydrogen or halogen atom or an alkyl radical with 1 to 6 carbon atoms, and
Y represents a hydrogen or halogen atom, or an alkyl radical with 1 to 6 carbon atoms or a halogenoalkyl radical with 1 to 6 carbon atoms and 1 to 5 halogen atoms.

3. A compound according to claim 2, in which
R¹ represents a fluorine, chlorine, bromine or iodine atom or a methyl radical,
R² represents a hydrogen, fluorine, chlorine, bromine or iodine atom,
X represents an oxygen or sulphur atom,
Y represents a hydrogen or chlorine atom or a methyl or trifluoromethyl radical and
A represents an alkylene radical which has up to 2 carbon atoms and is substituted by fluorine and optionally substituted by chlorine.

4. A compound according to claim 3, in which
R¹ represents a fluorine, chlorine or bromine atom or a methyl radical,
R² represents a hydrogen, fluorine, or chlorine atom,
Y represents a hydrogen or chlorine atom or a methyl or CF₃ radical and
A represents a difluoromethylene radical, or an ethylene radical which is substituted by 3 or 4 fluorine atoms or by 3 fluorine atoms and 1 chlorine atom.

5. A compound according to claim 1, wherein such compound is N-2,6-difluorobenzoyl-N'-(2,2,3-trifluoro-3-chloro-1,4-benzodioxin-6-yl)-urea of the formula

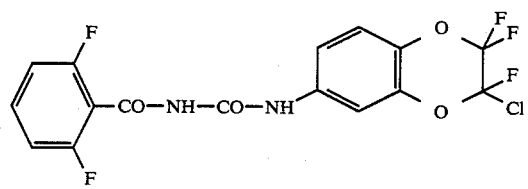

6. A compound according to claim 1, wherein such compound is N-(2-chloro-6-fluoro-benzoyl)-N'-(2,2,3-trifluoro-1,4-benzodioxin-6-yl)-urea of the formula

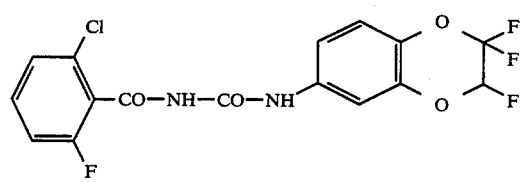

7. A compound according to claim 1, wherein such compound is N-2,6-difluorobenzoyl-N'-(2,2-difluoro-benzodioxol-5-yl)urea of the formula

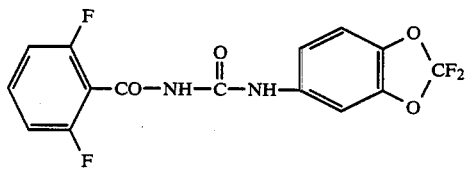

8. A compound according to claim 1, wherein such compound is N-2,6-difluorobenzoyl-N'-(2,3,3-trifluoro-7-chloro-1,4-benzodioxin-6-yl)-urea of the formula

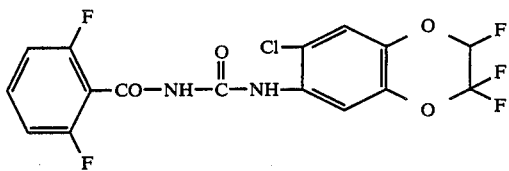

9. A compound according to claim 1, wherein such compound is N-(2,-chloro-6-fluoro-benzoyl)-N'-(2,2,3-trifluoro-3-chloro-1,4-benzodioxin-6-yl)-thiourea of the formula

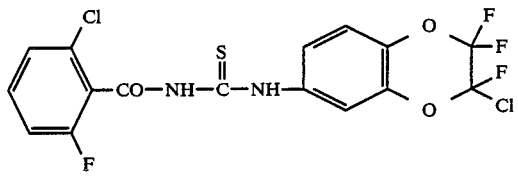

10. A compound according to claim 1, wherein such compound is N-2,6-difluorobenzoyl-N'-(2,2,3-trifluoro-3-chloro-1,4-benzodioxin-6-yl)-thiourea of the formula

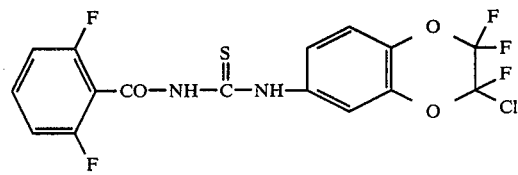

11. A pesticidal composition, characterized in that is contains as active ingredient a pesticidally effective amount of a compound according to claim 1 in admixture with a diluent.

12. A method of combating pests comprising applying to the pests, or to a habitat thereof, a pesticidally effective amount of a compound according to claim 1.

13. The method according to claim 12, wherein said compound is

N-2,6-difluorobenzoyl-N'-(2,2,3-trifluoro-3-chloro-1,4-benzodioxin-6-yl)-urea,
N-(2-chloro-6-fluoro-benzoyl)-N'-(2,2,3-trifluoro-1,4-benzodioxin-6-yl)-urea,
N-2,6-difluorobenzoyl-N'-(2,2-difluoro-benzodioxol-5-yl)urea,
N-2,6-difluorobenzoyl-N'-(2,3,3-trifluoro-7-chloro-1,4-benzodioxin-6-yl)-urea,
N-(2-chloro-6-fluoro-benzoyl)-N'-(2,2,3-trifluoro-3-chloro-1,4-benzodioxin-6-yl)-thiourea,
N-2,6-difluorobenzoyl-N'-(2,2,3-trifluoro-3-chloro-1,4-benzodioxin-6-yl)-thiourea or
N-(2-fluorobenzoyl)-N'-(2,2,3,3-tetrafluoro-1,4-benzodioxin-6-yl)-thiourea.

14. A compound selected from the group consisting of

N-2,6-difluorobenzoyl-N'-(2,2,3-trifluoro-3-chloro-1,4-benzodioxin-6-yl)-urea,
N-(2-chloro-6-fluoro-benzoyl)-N'-(2,2,3-trifluoro-1,4-benzodioxin-6-yl)-urea,
N-2,6-difluorobenzoyl-N'-(2,2-difluoro-benzodioxol-5-yl)urea,
N-2,6-difluorobenzoyl-N'-(2,3,3-trifluoro-7-chloro-1,4-benzodioxin-6-yl)-urea,
N-(2,-chloro-6-fluoro-benzoyl)-N'-(2,2,3-trifluoro-3-chloro-1,4-benzodioxin-6-yl)-thiourea,
N-2,6-difluorobenzoyl-N'-(2,2,3-trifluoro-3-chloro-1,4-benzodioxin-6-yl)-thiourea and
N-(2-fluorobenzoyl)-N'-(2,2,3,3-tetrafluoro-1,4-benzodioxin-6-yl)-thiourea.

15. A compound according to claim 1, wherein such compound is N-(2-fluorobenzoyl)-N$^1$-(2,2,3,3-tetrafluoro-1,4-benzodioxin-6-yl)-thiourea of the formula

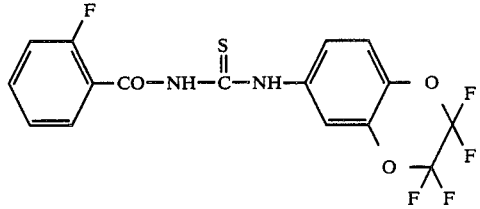

* * * * *